United States Patent
Kroll

(10) Patent No.: US 6,208,899 B1
(45) Date of Patent: Mar. 27, 2001

(54) IMPLANTABLE CARDIOVERSION DEVICE WITH AUTOMATIC FILTER CONTROL

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/396,568

(22) Filed: Sep. 15, 1999

(51) Int. Cl.$^7$ .................................................. A61N 1/39
(52) U.S. Cl. ................................................... 607/9
(58) Field of Search ............................. 600/515, 516, 600/517, 518, 510; 607/9

(56) References Cited

U.S. PATENT DOCUMENTS

| 4,184,493 | 1/1980 | Langer et al. ........................ 128/419 |
| 4,381,786 | * 5/1983 | Duggan . |
| 4,903,699 | 2/1990 | Baker, Jr. et al. .................... 128/419 |
| 4,967,747 | 11/1990 | Carroll et al. ........................ 128/419 |
| 5,188,117 | 2/1993 | Steinhaus et al. .................... 128/708 |
| 5,339,820 | 8/1994 | Henry et al. ......................... 128/696 |
| 5,395,393 | 3/1995 | Wickham ................................ 607/5 |
| 5,404,880 | 4/1995 | Throne ................................ 128/705 |
| 5,431,685 | 7/1995 | Alt ......................................... 607/6 |
| 5,492,128 | 2/1996 | Wickham .............................. 128/696 |
| 5,558,097 | 9/1996 | Jacobson et al. .................... 128/705 |

FOREIGN PATENT DOCUMENTS

| 93108031 | 5/1993 | (EP) . |
| PCT/US92/ 04648 | 6/1992 | (WO) . |

* cited by examiner

*Primary Examiner*—Scott M. Getzow

(57) ABSTRACT

An implantable cardioversion device includes a sensor for sensing intrinsic cardiac activity in a cardiac chamber, for example, the ventricle, and filtering the same using a bandpass filter having an adjustable center frequency. During normal sinus rhythm, the filter center frequency is set to correspond to the center frequency of normal R waves. If a sinus rhythm is not sensed, the filter center frequency is adjusted toward the frequency characteristic of an abnormal cardiac condition, such as ventricular fibrillation. The adjustable filter may be incorporated into an automatic threshold control system so that both the filter center frequency and the threshold are varied in synchrony. The adjustable filter may also be incorporated with an automatic gain control system wherein the filter center frequency and the gain are adjusted simultaneously.

41 Claims, 7 Drawing Sheets

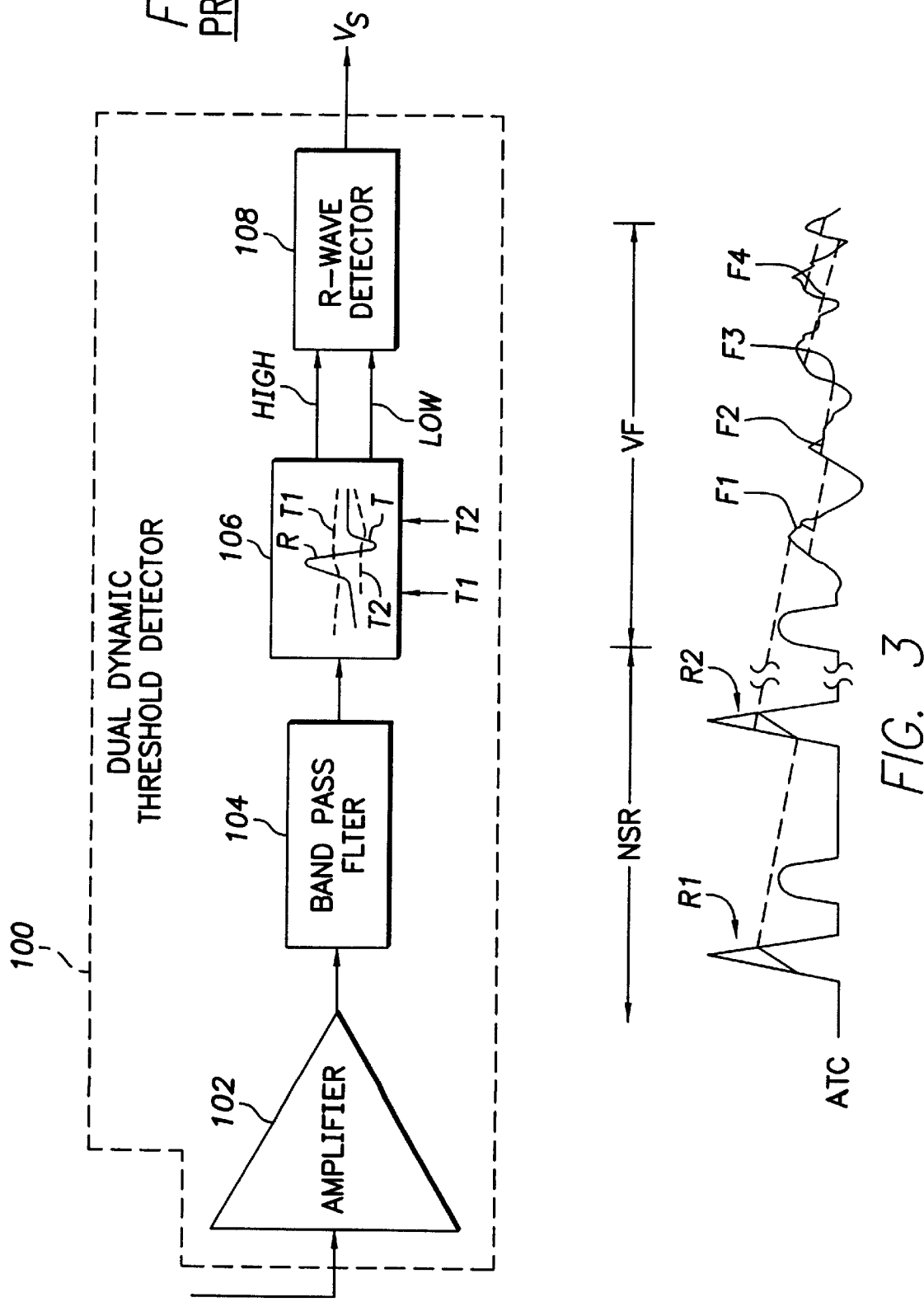

FIG. 6

IMPLANTABLE CARDIOVERSION DEVICE WITH AUTOMATIC FILTER CONTROL

FIELD OF THE INVENTION

This invention pertains to implantable cardioversion devices (ICDs) which sense a dangerous cardiac arrhythmia and, in response, provide therapy to the patient's heart to revert it to a normal sinus rhythm. More specifically, the present invention pertains to a device which includes a bandpass filter with a variable center frequency for detecting and categorizing intrinsic cardiac activity.

BACKGROUND OF THE INVENTION

As used herein, the term "arrhythmia" refers to any abnormal heart rhythm that may be dangerous to the patient and specifically includes fibrillation, tachycardias, supraventricular tachycardias (SVT), ventricular tachycardias (VT), ventricular fibrillation and flutter (VF), and bradycardia. As further used herein, the term "therapy"0 refers to any means used by the ICD device to restore normal heart rhythm, such as defibrillation, cardioversion, anfitachycardia pacing and drug infusion. The disclosed invention has application to ICD devices which treat tachyarrhythmias (abnormally high heart rates).

A modem conventional bradycardia pacemaker has a sensing mechanism to enable the device to inhibit pacing when the heart is beating normally. Implantable tachyarrhythmia devices must also sense the heart's intrinsic electrical activity, known as the electrocardiogram (ECG), to determine whether the patient needs treatment. ECGs exhibit highly variable amplitudes and frequencies as the cardiac activity changes from normal sinus rhythms (NSR) to other abnormal rhythms such as ventricular tachycardia and ventricular fibrillation.

U.S. Pat. No. 4,184,493 to Langer et al., which issued on Jan. 22, 1980, and is entitled "Circuit for Monitoring a Heart and for Effecting Cardioversion of a Needy Heart", describes a sensing circuit that automatically adjusts to the amplitude of the heart's electrical signal using an automatic gain control (AGC) system.

Another form of sensing system with AGC is described in U.S. Pat. No. 4,903,699 to Baker et al., which issued on Feb. 27, 1990, and is entitled "Implantable Cardiac Stimulator With Automatic Gain Control". The Baker et al. patent uses a system of comparators and adjustable thresholds to optimally detect the ECG signal.

Both of the foregoing patents describe systems which also filter the ECG signal to remove low frequency noise and artifacts. In addition, high pass filtering is used in these patents to reduce sensing of T waves during normal sinus rhythm (NSR). However, high frequency filtering also attenuates VF signals and makes it difficult to detect the same, especially since VF signals have low amplitudes as compared to signals during NSR.

Another control scheme is disclosed in commonly assigned U.S. Pat. No. 5,395,393, incorporated herein by reference. This patent discloses an ICD in which a different sensing circuit is provided for sensing tachyarrhythmia (including supraventricular tachycardia), ventricular tachycardia or ventricular fibrillation, and for differentiating these conditions from normal sinus rhythm. More specifically, a sensor circuit includes an amplifier, a bandpass filter having a fixed center frequency, a dual dynamic threshold detector and a classifier for detecting tachyarrhythmia using a clustering algorithm. This type of control is commonly referred to as automatic threshold control (ATC) and while it generally works well to differentiate the various types of tachyarrhythmia from random noise, it is generally not effective in detecting tachyarrhythmia in the presence of electromyography signals (EMG) generated by muscles in the chest area, or noise due to standard 50 or 60 Hz power sources.

SUMMARY OF THE INVENTION

In view of the above mentioned disadvantages of the prior art, it is an objective of the present invention to provide an implantable cardioversion device (ICD) with an improved sensing circuit that can detect arrhythmias quickly and accurately.

A further objective is to provide an ICD which is capable of detecting dangerous cardiac conditions in the presence of extraneous signals such as noise from standard power supplies or muscular activity.

Yet a further objective is to provide a system which can be implemented easily with minimal changes to existing sensing circuits.

Other objectives and advantages of the invention shall become apparent from the following description.

Briefly, an implantable cardiac stimulator constructed in accordance with this invention includes a sensor for sensing intrinsic cardiac activity in the heart of a patient and a detector for detecting an abnormal condition of the heart based on this sensed intrinsic activity. The stimulator further includes a therapy generator for automatically applying a preselected therapy when the abnormal condition is detected to cause the heart to revert quickly and reliably to a normal sinus rhythm. Preferably the sensor includes an amplifier for amplifying the signals from the heart and a filter for filtering the signals prior to providing the same to the detector. Importantly, the filter has a programmable or adjustable center frequency fc. A controller is also provided to control the center frequency fc of the filter.

It has been found that intrinsic signals sensed during normal sinus rhythm and during ventricular fibrillation have different characteristic frequency spectra. More specifically, the spectrum for normal sinus rhythm has a center frequency which is higher than the center frequency of the spectrum characterizing ventricular fibrillation (fvf).

Therefore, during a normal sinus rhythm period, the center frequency of the filter in embodiments of the present invention is set to correspond to the center frequency (fnsr) of sinus rhythm R waves. If ventricular fibrillation is suspected, for example, because R waves characteristic of a normal sinus rhythm are not detected, the center frequency fc is changed to fvf. Thus, the filter is tuned automatically so that it is optimized to detect ventricular fibrillation waves while rejecting or at least de-emphasizing extraneous noise signals produced, for example, by muscle contractions in the chest area and/or noise from external 50 or 60 Hz power supplies. After the heart chamber reverts to normal sinus rhythm, the center frequency of the filter is returned to its original value.

In this manner, the condition of the patient's heart is quickly determined and therefore appropriate therapy can be applied effectively.

Preferably, the center frequency fc is changed gradually from one value to the other.

In one embodiment of the invention, an automatic threshold control (ATC) scheme is used. In this embodiment, the filtered output is fed to a comparator for comparison with a threshold T which is a time varying parameter. More particularly, the threshold T is also changed at the same time that the center frequency fc of the filter is changed. Preferably, the threshold T is decreased when fc is decreased.

In another embodiment of the invention an automatic gain control (AGC) scheme is used. In this embodiment, the gain of the input amplifier is raised as the center frequency fc of the filter is lowered.

BRIEF DESCRIPTION OF THE DRAWINGS

FIG. 2 shows a first prior art sensing circuit incorporating an automatic threshold control (ATC) scheme;

FIG. 3 shows graphically the operation of the system of FIG. 2;

FIG. 6 shows a block diagram of an implantable cardioversion device constructed in accordance with the present invention;

DETAILED DESCRIPTION OF THE INVENTION

Figure 1A:
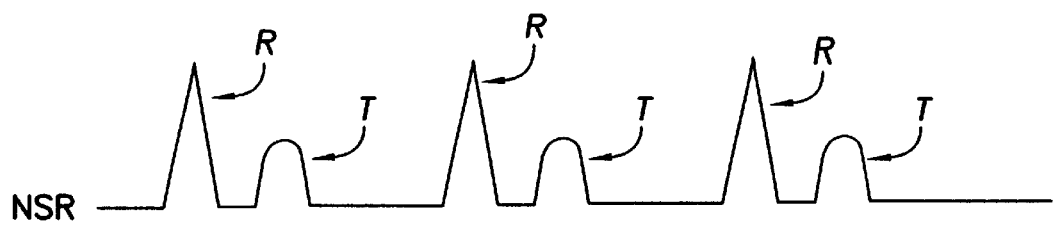
FIG. 1A shows a somewhat stylistic ECG that is characteristic of cardiac activity with normal sinus rhythm.
Figure 1B:
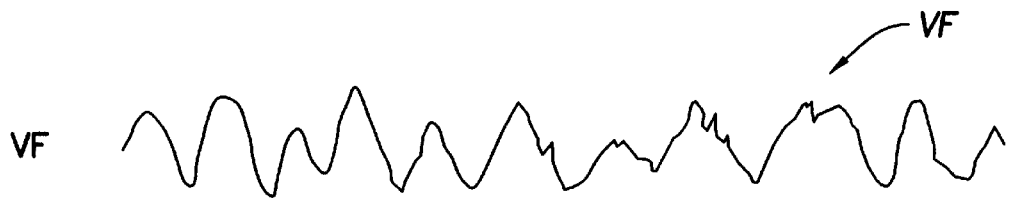
FIG. 1B shows an ECG that is characteristic of ventricular fibrillation.
Figure 1C:
FIG. 1C shows a typical EMG signal.
Figure 1D:
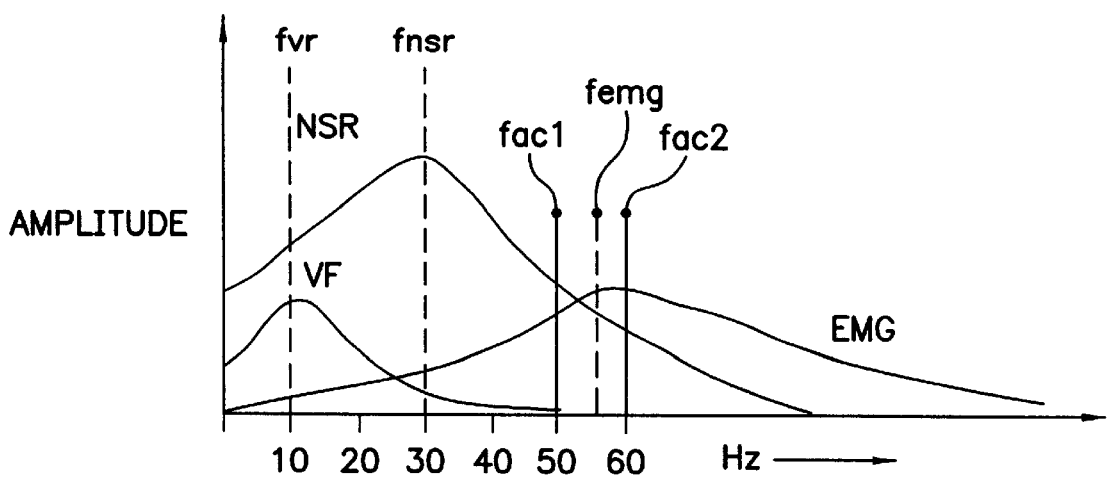
FIG. 1D shows comparatively the intensity and spectral distribution of the various signals sensed by an ICD.

FIGS. 1A, 1B and 1C show various intrinsic activities that may be sensed in the ventricle. FIGS. 1B and 1C have a vertical scale which is an order of magnitude smaller than the vertical scale of FIG. 1A. The frequency spectrum and comparative amplitudes are shown in FIG. 1D.

FIG. 1A shows, in a somewhat stylized manner, sequential R waves followed by T waves characteristic of normal sinus rhythm (NSR).

FIG. 1B shows a waveformn characteristic of ventricular fibrillation (VF). As seen in this figure, this waveformn is very ragged and apparently chaotic.

FIG. 1C shows a waveform associated with muscle activity (EMG) in the chest area, for example, when a patient lifts his arm above his heart or lifts any weight.

FIG. 1D shows the frequency spectra for the waveforms of FIGS. 1A–1C. The center frequencies for these waveforms are indicia in the following table, together with their approximate frequencies:

| Waveform Description | Center Frequency |
|---|---|
| Normal Sinus Rhythm | fnsr (~30 Hz) |
| Ventricular Fibrillation | fvf (~10 Hz) |
| Electromyogram (EMG) | femg (~56 Hz) |
| 50 Cycle AC Noise | fac 1 (50 Hz) |
| 60 Cycle AC Noise | fac 2 (60 Hz) |

As demonstrated by FIGS. 1A–1D, the intrinsic signals sensed during ventricular fibrillation are much smaller than those sensed during NSR and they are the same order of magnitude as the EMG signals.

Ideally, an implantable cardioversion device (ICD) quickly senses an abrupt change in the state of the patient's heart by accurately differentiating between normal sinus rhythm (NSR) and ventricular fibrillation (VF), while ignoring extraneous signals, including EMG and noise from 50 Hz or 60 Hz power supplies.

Referring now to FIG. 2, a typical prior art sensor 100 using automatic threshold control (ATC) includes an amplifier 102, a fixed center frequency bandpass filter 104, a threshold detector 106 and an R wave detector 108. As described in more detail in U.S. Pat. No. 5,395,393, the signal from an electrode implanted, for example, in the ventricle is amplified by amplifier 102. After filtering, the signal is fed to a dynamic threshold detector 106. This detector compares the incoming signal to two dynamic time dependent thresholds T1 and T2. As clearly seen in FIG. 2, both thresholds T1 and T2 initially rise after an R wave is detected, and then they both slowly decay to a lower level. The rate of decay of T1 must be slow enough to ensure that a T wave is not sensed. In the scheme of FIG. 2, when the sensed signals exceeds T1 or drops below T2, a corresponding signal High and Low is generated to R wave detector 108. The detector 108 then uses a clustering algorithm to detect the R wave and generate a corresponding $V_s$ (ventricular sense) signal. In other known ATC schemes, a single time varying threshold level is used in conjunction with other known techniques to detect the R wave.

FIG. 3 shows an interval of NSR followed by an interval of VF and the corresponding changes in the level T1 in accordance with ATC (of the single threshold type). Once again, the amplitude of the VF signals during the ventricular fibrillation interval has been emphasized for the sake of clarity. As it can be seen from this figure, after the first R wave is sensed (R1), the threshold T1 gradually decreases until the second R wave (R2). When the VF interval starts, the threshold T1 decreases (i.e., the sensitivity of the system increases) since no R waves are sensed until the signals F1, F2 . . . are detected.

A problem with this scheme is best appreciated from FIG. 1D which shows the spectral content and relative intensities of the NSR, VF and EMG signals, as well as noise from 50 Hz or 60 Hz power sources. These signals overlap considerably in the frequency domain, especially at frequencies higher than 25 Hz. In fact, in this frequency range, the EMG signals clearly have a higher intensity then the VF signals. Therefore, the system of FIG. 2 may incorrectly interpret power signals or power line noise since both of these have higher amplitudes than the VF signals.

Figure 4:
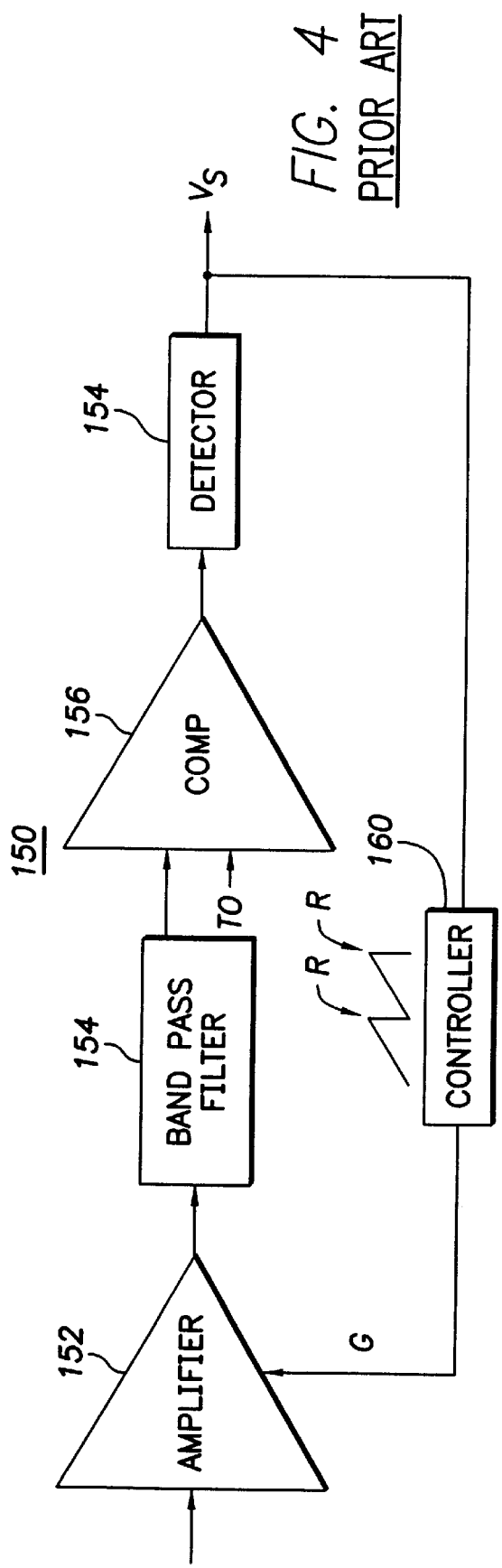
FIG. 4 shows a second prior art sensing circuit incorporating an automatic gain control (AGC) scheme.

FIG. 4 shows a typical, somewhat simplified, AGC control scheme. In this figure a sensor system 150 consists of an amplifier 152 having a variable gain G. The output of the amplifier 152 is fed to a fixed center frequency bandpass filter 154 and then to a comparator 156. This comparator 156 compares the output of amplifier 152 to a predetermined threshold T0. The output of comparator 156 is fed to an R wave detector 158 which uses a further time-related criteria (such as blanking periods) to detect R waves and generate a corresponding $V_s$ signal. The $V_s$ signal is also fed to a controller 160 which generates a time varying gain G. This gain slowly increases with time and is slowly decreased after an R wave is sensed.

Figure 5:
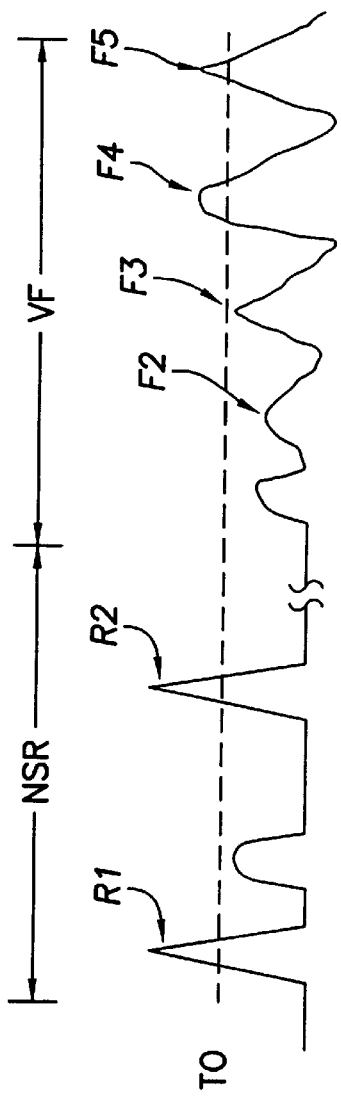
FIG. 5 shows graphically the operation of the system of FIG. 4.

The operation of the system 150 is shown in FIG. 5. The waves R1 and R2 are sensed in the normal manner. During the VF period, the gain G increases gradually thereby boosting the peak amplitudes of the VF signals such as F1, F2, F3 . . . until they are detected. This system has the same deficiencies as the ATC system shown in FIGS. 2 and 3 and can additionally suffer from control loop instabilities.

Figure 6:
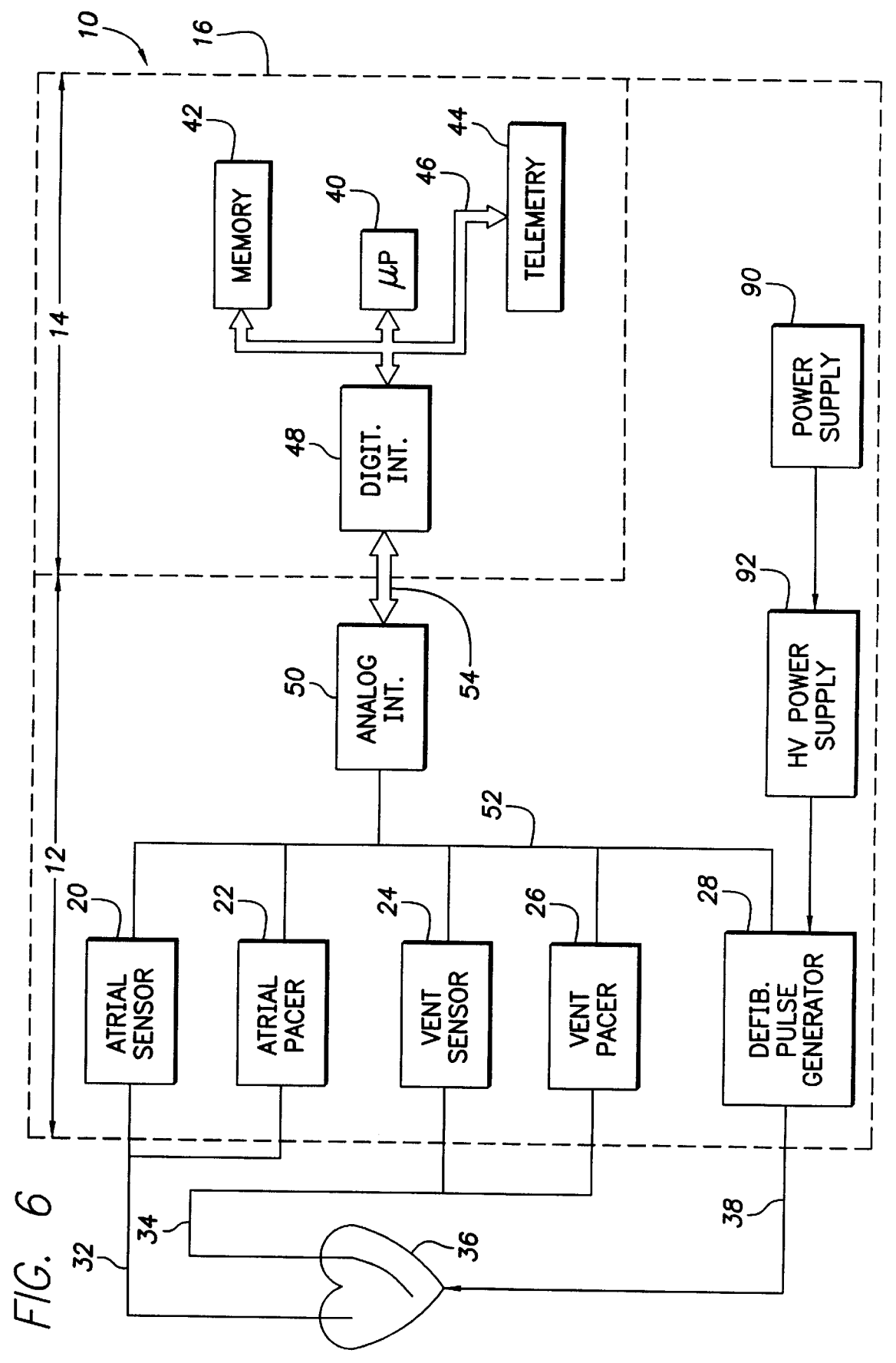

FIG. 6 shows a block diagram for an implantable cardioversion device (ICD) in accordance with the present invention, which, in this case, is incorporated into a dual chamber pacemaker 10 and will be described as a subsystem thereof. However, it should be understood that the ICD need not be part of a pacemaker. Nor must the system include pacing in both chambers. In the illustrated embodiment, pacemaker 10 includes an analog section 12 and a digital section 14 incorporated in an hermetic implantable housing 16. The analog section 12 includes an atrial sensor 20, an atrial pacer 22, a ventricular sensor 24, a ventricular pacer 26 and a defibrillation pulse generator 28.

Leads 32 and 34 connect the pacemaker 10 to the atrial and ventricular chambers of the heart 36, respectively. The atrial and ventricular sensors 20, 24 are used to sense intrinsic events in the corresponding cardiac chambers (i.e., signals originating in the patient's heart), and the atrial and ventricular pacers 22, 24 provide respective atrial and ventricular pacing via leads 32 and 34, for example, in a DDD or DDDR mode, well known in the art. Cardioversion, for example by antitachycardia pacing (ATP) pulses, may be generated by atrial and ventricular pacers 22, 26 in response to a therapy generator (preferably within the digital section 14) configured to delivered a prescribed therapy regime. If ATP fails, the therapy generator will cause the pulse generator 28 to deliver defibrillation shocks via lead 38. Energy for the pacemaker 10 is provided by a power supply 90. A separate high voltage supply 92 is used to feed the defibrillator pulse generator 28.

The operation of the pacemaker 10 is controlled by the digital section which preferably consists of a microprocessor 40 and a memory 42. The memory 42 holds programming information for the microprocessor 40 and is also used for data logging. Initial programming, as well as any programming updates and subsequent downloading of logged data, take place through a telemetry circuit 44. An internal bus 46 couples the memory 42, microprocessor 40 and telemetry circuit 44 together and to a digital section interface 48. Similarly, the various elements of the analog section 12 described above are connected to an analog section interface 50 by an internal bus 52. Communication between sections 12 and 14 is established through a bus 54.

Figure 7:
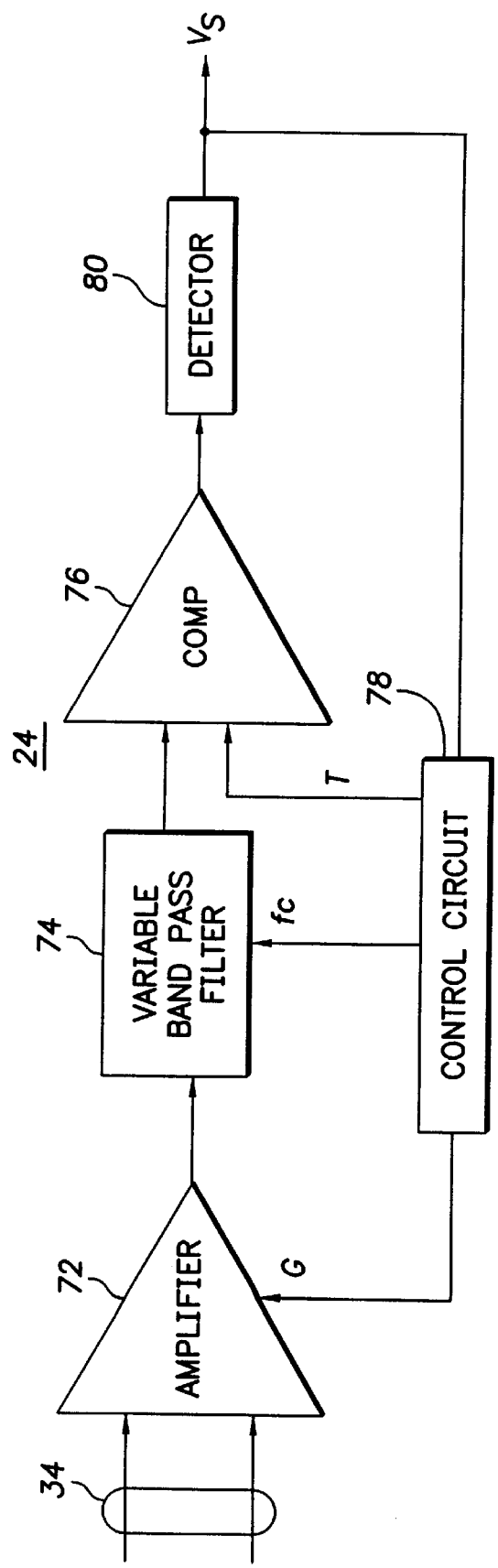
FIG. 7 shows a block diagram of a sensing system for sensing tachyarrhythmia for the device of FIG. 6.

Importantly, ventricular sensor 24 includes, as shown in FIG. 7, an amplifier 72, a variable bandpass filter 74 and a comparator 76. The sensor 24 also includes a control circuit 78 and a detector 80. It should be understood that some of the elements shown as discrete circuits in FIG. 7 may actually be implemented by software in the digital section 14. The intrinsic signals sensed in the ventricle are fed to amplifier 72. This amplifier 72 may have a variable gain G, if desired, as set forth above. However, in this embodiment, it is assumed that its gain is constant. The output of amplifier 72 is fed to variable bandpass filter 74. This filter has a variable center frequency fc controlled by control circuit 78. During NSR, the center frequency of the filter 74 is set to fnsr, i.e., the frequency of the R waves sensed during normal sinus rhythm. This frequency fnsr is dependent on a number of different criteria, including the characteristics of the electrodes, their position within the ventricle and so forth. In FIG. 1D, fnsr is shown at about 30 Hz.

The output of the filter 74 is fed to a signal processor portion comprised of a comparator 76 and a detector 80. The comparator 76 compares the received signal to a time varying threshold T. The output of the comparator 76 is fed to detector 80 which analyzes the output of the comparator and generates a signal $V_s$ indicative of an intrinsic ventricular contraction. This determination may be made in a number of different ways which are known in the art and which do not limit the present invention.

Importantly, the signal $V_s$ is also fed to control circuit 78. The control circuit 78 monitors the generation of the signal $V_s$ and, in response, controls the center frequency fc of filter 74. Optionally, the control circuit 78 also generates a variable gain G for amplifier 72, as discussed in more detail below.

Figure 8A:
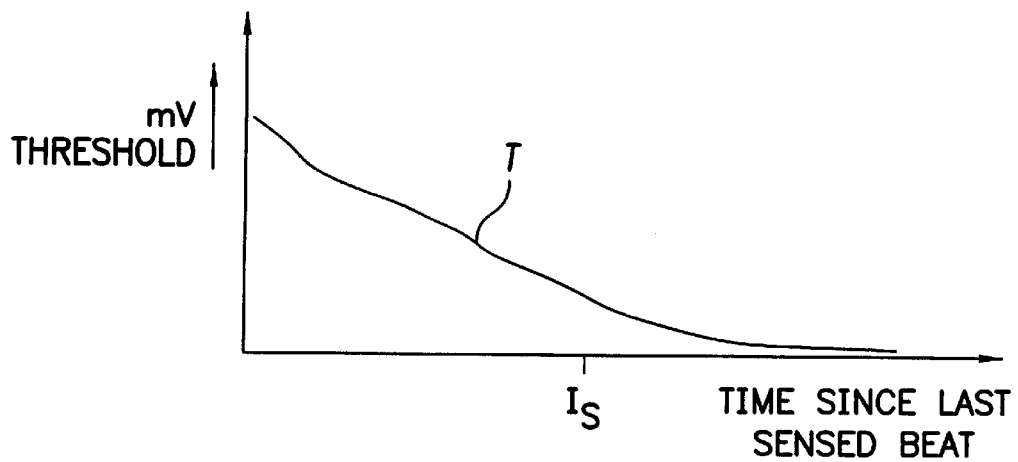
FIG. 8A shows the threshold variation for the sensing system of FIG. 7.
Figure 8B:
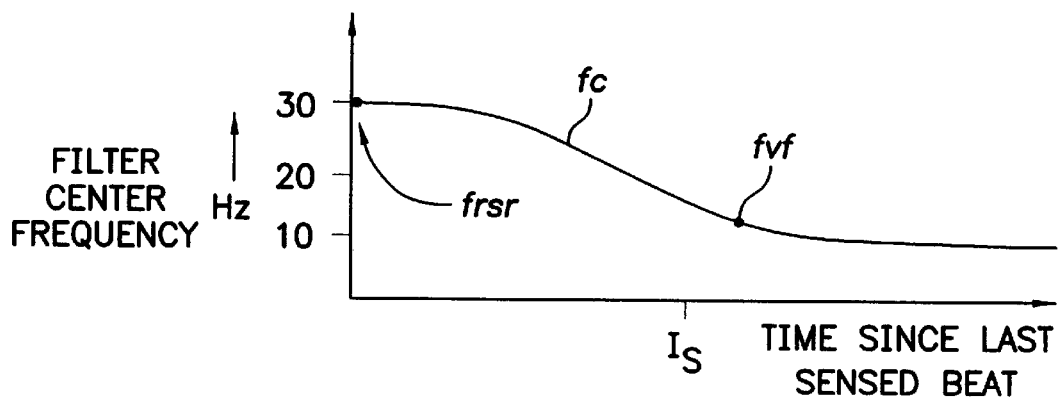
FIG. 8B shows the center frequency variation for the filter in the sensing system of FIG. 7.
Figure 9:
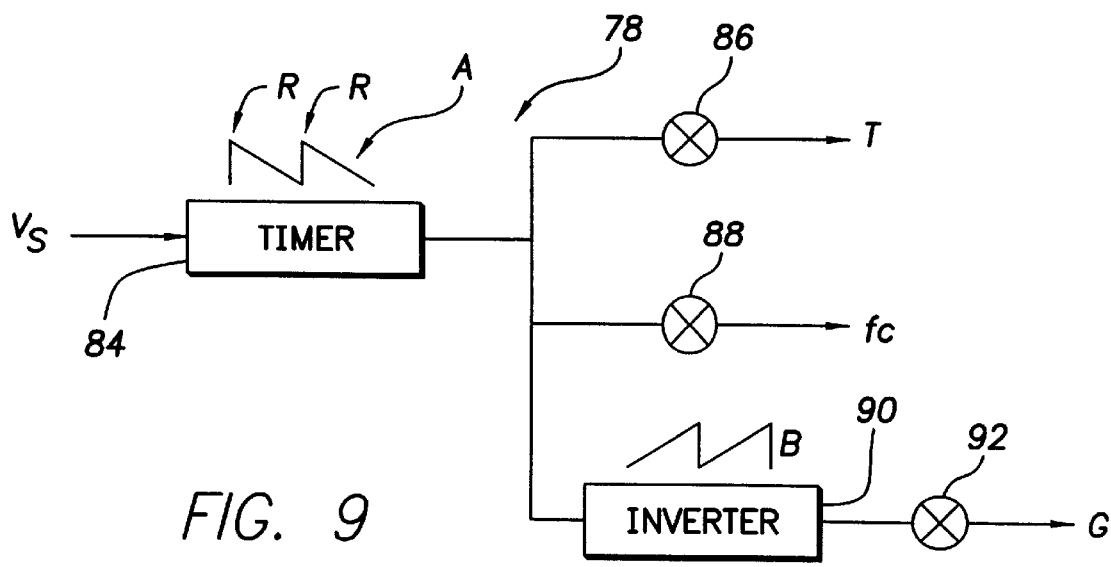
FIG. 9 shows a block diagram for a controller for the sensing system of FIG. 7.

As shown in detail in FIG. 9, the control circuit 78 includes a timer 84 which is triggered by R waves sensed by detector 80. As indicated by sawtooth shaped waveform A, each time an R wave is sensed, the timer starts waveform A at its maximum amplitude. The signal represented by waveform A is then fed to multipliers 86 and 88. These multipliers multiply this signal by appropriate scaling constants to generate respectively the threshold T and the center frequency fc. Therefore, these parameters slowly decrease from a peak value, as shown in FIGS. 8A and 8B, respectively. For instance, referring to FIG. 1D, the maximum value of fc for detecting normal sinus rhythm is about 30 Hz (fnsr). The center frequency fc then decays in about 1 second to about 10 Hz (fvf) for detecting VF.

Figure 8C:
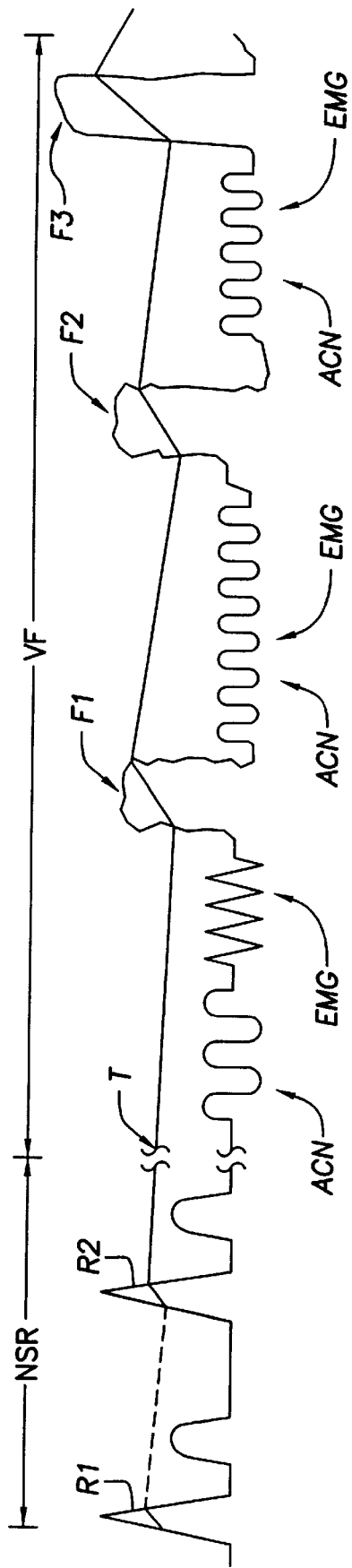
FIG. 8C shows graphically the operation of the sensing system of FIG. 7.

The result of shifting T and fc can be seen in FIG. 8C. Initially during an NSR period, R waves R1, R2 are detected with fc and T being at their maximum values shown in FIGS. 8A and 8B, respectively. When VF sets in, the value of T and fc both slowly decay. As can be clearly seen in FIG. 8C, the downward shift of fc causes the AC noise ACN from external power supplies and EMG noise to be de-emphasized since they have a higher frequency than fc. More specifically, as fc gets smaller and smaller, these two noise parameters get lower and lower as shown. Meanwhile, since fc approaches the center frequency fvf characteristic of VF, the amplitude of the signals (into the comparator) gets higher and higher allowing the comparator to detect fibrillation pulses F1, F2, F3, etc.

In this manner, the system is able to differentiate quickly and accurately between noise (such as ACN and EMG) and VF.

In FIG. 9, the threshold parameter T is generated as a simple sawtooth. It should be understood that a more complex waveform may be generated as well. In addition, a double threshold scheme may also be used as taught in U.S. Pat. No. 5,395,393.

In addition to changing the threshold T, the gain G of amplifier 72 (FIG. 7) may also be adjusted by control circuit 78. More specifically, as shown in FIG. 9, for this purpose the output of timer 84 (represented by waveform A) is first fed to an inverter 90. The purpose of this inverter is to invert the signal represented by waveform A to form a signal indicated by waveform B. This inversion is necessary because the gain of amplifier 72 must be raised for the detection of VF. The inverted signal (shown as waveform B) is then scaled by multiplier 92 to generate the gain signal G. While raising the amplification factor G counteracts to some extent the de-emphasis of the noise signals ACN and EMG produced by the filter 74, this effect is not very significant since the deemphasis produced by the filter 74 is discriminatory. That is, as the center frequency fc is shifted downward, the amplitude of the noise components is reduced more than the linear amplification produced by raising the gain G.

After defibrillation therapy is applied, the cardiac chamber usually reverts to normal sinus rhythm. This event is detected by detector 80. In response, the control circuit reverses the process(es) described above and returns the center frequency fc, threshold T and/or gain G to their original (i.e., normal sinus rhythm values).

While the invention herein disclosed has been described by means of specific embodiments and applications thereof, numerous modifications and variations could be made thereto by those skilled in the art without departing from the scope of the invention as set forth in the claims.

What is claimed is:

1. An implantable cardiac stimulator configured to detect the presence of a normal sinus rhythm or an abnormal cardiac condition of a patient's heart in response to a signal from a lead coupled to the patients heart, the stimulator comprising:
    an amplifier for receiving and amplifying a signal from the lead in the patient's heart;
    a variable bandpass filter for receiving the amplified signal, the filter having a filter center frequency dynamically configurable to facilitate passing a filtered signal corresponding to a normal sinus rhythm or an abnormal cardiac condition;
    a signal processor for processing the filtered signal to generate a detected output signal corresponding to the presence of a normal sinus rhythm or an abnormal cardiac condition; and
    a control circuit for adjusting the center frequency of the variable bandpass filter in response to the detected output signal of the signal processor to facilitate detection of an abnormal cardiac condition.

2. The stimulator of claim 1, wherein at least one abnormal cardiac condition of the patient's heart corresponds to fibrillation.

3. The stimulator of claim 1, wherein a normal sinus rhythm is comprised of periodic R waves and has a first center frequency and a signal corresponding to an abnormal cardiac condition has a second center frequency and whereby the control circuit causes the filter center frequency to adjust between the first center frequency and the second center frequency to facilitate detection of an abnormal cardiac condition.

4. The stimulator of claim 3, wherein the control circuit causes the filter center frequency to continuously adjust between the first center frequency and the second center frequency following each R wave to facilitate detection of an abnormal cardiac condition.

5. The stimulator of claim 3, wherein the filter center frequency adjusts linearly between the first center frequency and the second center frequency following each R wave to facilitate detection of an abnormal cardiac condition.

6. The stimulator of claim 3, wherein the center frequency adjusts linearly between the first and second center frequencies over a time period of approximately one second following each R wave.

7. The stimulator of claim 1, wherein the amplifier can amplify the signal from the lead by a gain factor and the gain factor is controllable by the control circuit.

8. The stimulator of claim 7, wherein the gain factor is continuously controllable between a first gain factor corresponding to a normal sinus rhythm and a second gain factor corresponding to an abnormal cardiac condition.

9. The stimulator of claim 7, wherein the control circuit causes the gain factor to increase in coordination with a decrease in the center frequency of the variable bandpass filter.

10. The stimulator of claim 1, wherein the signal processor is sensitive to signals above a threshold level and the threshold level is controllable by the control circuit.

11. The stimulator of claim 10, wherein the threshold level is continuously adjustable between a first threshold level corresponding to a normal sinus rhythm and a second threshold level corresponding to an abnormal cardiac condition.

12. The stimulator of claim 11, wherein the control circuit causes the threshold level to decrease in coordination with a decrease in the center frequency of the variable band pass filter.

13. The stimulator of claim 1, wherein the stimulator includes cardioverter circuitry for generating therapy to revert the patient's heart to a normal sinus rhythm when an abnormal cardiac condition is detected.

14. An implantable cardioversion device for detecting and reverting ventricular fibrillation in a patient's heart, the device comprising:
    a ventricular sensor for sensing intrinsic ventricular activity and generating a corresponding sense signal; the ventricular sensor including:
        a filter for filtering the sense signal to generate a filtered signal, wherein the filter has an adjustable center frequency;
        a detector for detecting ventricular fibrillation or normal sinus rhythm based on the filtered signal; and
        a controller for adjusting the center frequency to a value corresponding to the most recently detected normal sinus rhythm; and
    a therapy generator for generating a prescribed therapy in response to the detector detecting ventricular fibrillation in the patient's heart.

15. The device of claim 14, wherein the detector further includes a comparator for comparing the filtered signal to a threshold level.

16. The device of claim 14, wherein the threshold level is time varying.

17. The device of claim 14, wherein the threshold level has a first threshold value corresponding to a normal sinus rhythm and a second value corresponding to a ventricular fibrillation.

18. The device of claim 14, wherein the filter center frequency has a first filter frequency value corresponding to a normal sinus rhythm and a second filter frequency value corresponding to a ventricular fibrillation.

19. The device of claim 18, wherein the controller is configured to set the filter center frequency to the first filter frequency value in the presence of a normal sinus rhythm and to adjust the filter center frequency toward the second filter frequency value in the absence of a normal sinus rhythm.

20. The device of claim 19, wherein the controller changes the filter center frequency gradually from the first to the second center frequency value.

21. The device of claim 19, wherein the controller changes the filter center frequency linearly from the first to the second frequency value.

22. The device of claim 19, wherein the controller changes the filter center frequency from the first to the second frequency value over a time period of about one second.

23. The device of claim 18, wherein the detector further includes a comparator for comparing the filtered signal to a threshold level.

24. The device of claim 23, wherein the threshold level is time varying.

25. The device of claim 23, wherein the threshold level has a first threshold value corresponding to a normal sinus rhythm and a second threshold value corresponding to a ventricular fibrillation.

26. The device of claim 25, wherein the controller is configured to set the filter frequency in a range between the first and the second frequency values and for setting the threshold in a range between the first and second threshold values.

27. The device of claim 26, wherein the controller gradually and cooperatively changes the center frequency and the threshold level.

28. A method of applying cardioversion therapy to a patient with an implantable cardioversion device coupled to the patient's heart, the method comprising the steps of:
  sensing an intrinsic signal in a cardiac chamber of the patient's heart to obtain a sensed signal;
  bandpass filtering the sensed signal to generate a filtered signal using a filter having a center frequency adjustable between a first frequency value corresponding to a normal sinus rhythm and a second frequency value corresponding to an abnormal cardiac condition;
  analyzing the filtered signal to detect a normal sinus rhythm condition;
  adjusting the center frequency toward the second value if a normal sinus rhythm is not detected to facilitate detecting the presence of an abnormal cardiac condition; and
  applying therapy in the presence of a detected abnormal cardiac condition.

29. The method of claim 28, wherein the second frequency value is selected to correspond to a ventricular fibrillation.

30. The method of claim 28, wherein the step of analyzing includes comparing the bandpassed signal to a sensing threshold value.

31. The method of claim 30, further comprising adjusting the threshold value dependent on the absence of a normal sinus rhythm.

32. The method of claim 30, wherein the sensing threshold is adjusted gradually from a first threshold value corresponding to a normal sinus rhythm toward a second threshold value corresponding to an abnormal cardiac condition in the absence of a normal sinus rhythm.

33. The method of claim 32, further comprising adjusting the gain value from a first gain level corresponding to a normal sinus rhythm toward a second gain level corresponding to an abnormal cardiac condition.

34. The method of claim 28, further comprising amplifying the sensed signal by a gain value.

35. A method of applying cardioversion therapy to a patient's heart with an implantable cardioversion device having an input bandpass filter with a center frequency adjustable between first and second frequency values, the method comprising the steps of:
  sensing an intrinsic signal in a chamber of the patient's heart to obtain a sensed signal;
  filtering the sensed signal with the input bandpass filter set at a first center frequency value corresponding to a normal sinus rhythm to generate a filtered signal;
  determining the presence of a normal sinus rhythm based on the filtered signal;
  adjusting the center frequency toward the second center frequency value corresponding to an abnormal cardiac condition if a normal sinus rhythm is not detected at the first center frequency value;
  determining the presence of an abnormal cardiac condition or a normal sinus rhythm; and
  changing the center frequency back to the first center frequency when a normal sinus rhythm is detected.

36. The method of claim 35, further comprising comparing the filtered signal to a threshold, the threshold being settable to a first threshold value corresponding to a normal sinus rhythm and a second threshold value corresponding to an abnormal cardiac condition.

37. The method of claim 36, wherein the threshold value adjusts from the first threshold value toward the second threshold value when a normal sinus rhythm is not detected.

38. The method of claim 37, further comprising adjusting the threshold from the second to the first threshold value when a normal sinus rhythm is detected.

39. The method of claim 36, further comprising amplifying the sensed signal by a gain setting settable between a first gain value corresponding to a normal sinus rhythm and a second gain value corresponding to an abnormal cardiac condition.

40. The method of claim 39, further comprising adjusting the gain setting from the first gain value toward the second gain value when a normal sinus rhythm condition is not detected.

41. The method of claim 40, further comprising changing the gain setting to the first gain value when a normal sinus rhythm is detected.

* * * * *